US011339961B2

(12) United States Patent
Leijssen (10) Patent No.: US 11,339,961 B2
(45) Date of Patent: May 24, 2022

(54) METHOD AND SYSTEM FOR PROTECTING A SURFACE AGAINST BIOFOULING

(71) Applicant: KONINKLIJKE PHILIPS N.V., Eindhoven (NL)

(72) Inventor: Jacobus Josephus Leijssen, Waare (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/277,334

(22) PCT Filed: Sep. 18, 2019

(86) PCT No.: PCT/EP2019/075007
§ 371 (c)(1),
(2) Date: Mar. 18, 2021

(87) PCT Pub. No.: WO2020/058335
PCT Pub. Date: Mar. 26, 2020

(65) Prior Publication Data
US 2021/0348753 A1     Nov. 11, 2021

(30) Foreign Application Priority Data

Sep. 20, 2018   (EP) .................................... 18195677

(51) Int. Cl.
*F21V 31/00* (2006.01)
*F21V 23/02* (2006.01)
*F21V 23/04* (2006.01)
(Continued)

(52) U.S. Cl.
CPC ................ *F21V 31/00* (2013.01); *A61L 2/10* (2013.01); *B08B 17/02* (2013.01); *F21V 23/02* (2013.01);
(Continued)

(58) Field of Classification Search
CPC ...... F21V 31/00; F21V 23/02; F21V 23/0442; H02J 50/10; H02J 50/402; H02J 50/90;
(Continued)

(56) References Cited

U.S. PATENT DOCUMENTS 5,643,424 A    7/1997  Riffe et al.
6,579,495 B1   6/2003  Maiden
(Continued)

FOREIGN PATENT DOCUMENTS

CN    101709191 B    8/2011
CN    107124041 A    9/2017
(Continued)

OTHER PUBLICATIONS

International Search Report and Written Opinion from PCT/EP2019/075007 dated Mar. 26, 2020.

*Primary Examiner* — Bao Q Truong (57) ABSTRACT

An anti-fouling lighting system is used for protecting a surface (16) against biofouling while the surface (16) is submerged in water. A non-contact water sensor (60) is used for sensing water thereby to detect whether or not a light source arrangement (26), or a portion of the light source arrangement (26), is submerged in water. The light source arrangement (26), or the portion of the light source arrangement (26), is controlled in dependence on the water sensor (60) output.

12 Claims, 4 Drawing Sheets

(51) Int. Cl.
*H02J 50/10* (2016.01)
*H02J 50/40* (2016.01)
*A61L 2/10* (2006.01)
*B08B 17/02* (2006.01)
*F21W 107/20* (2018.01)
*H02J 50/90* (2016.01)
*B63B 59/04* (2006.01)

(52) U.S. Cl.
CPC .......... *F21V 23/0442* (2013.01); *H02J 50/10* (2016.02); *H02J 50/402* (2020.01); *A61L 2202/11* (2013.01); *B63B 59/04* (2013.01); *F21W 2107/20* (2018.01); *H02J 50/90* (2016.02)

(58) Field of Classification Search
CPC ........ A61L 2/10; A61L 2202/11; B08B 17/02; F21W 2107/20; B63B 59/04
See application file for complete search history.

(56) References Cited

U.S. PATENT DOCUMENTS

| | | |
|---|---|---|
| 9,051,028 B2 | 6/2015 | Smith et al. |
| 9,611,016 B2 * | 4/2017 | Salters .................. G02B 6/0043 |
| 10,252,783 B2 * | 4/2019 | Salters .................... B08B 17/02 |
| 10,793,236 B2 * | 10/2020 | Salters .................... B63B 59/04 |
| 2010/0200756 A1 | 8/2010 | Maiden |
| 2012/0050520 A1 * | 3/2012 | Thoren .............. G02B 27/0006 |
| | | 348/81 |
| 2013/0334960 A1 | 12/2013 | Waffenschmidt et al. |
| 2016/0137276 A1 * | 5/2016 | Salters ............... G02B 19/0061 |
| | | 114/222 |
| 2017/0048934 A1 | 2/2017 | Sempel et al. |
| 2017/0190397 A1 | 7/2017 | Salters et al. |
| 2017/0334114 A1 | 11/2017 | Sticklus et al. |
| 2018/0134351 A1 * | 5/2018 | Salters ...................... A61L 2/10 |
| 2018/0154405 A1 * | 6/2018 | Janssen .................. B08B 17/00 |
| 2019/0207429 A1 | 7/2019 | Yoshida et al. |
| 2019/0014631 A1 | 10/2019 | Van Delden et al. |

FOREIGN PATENT DOCUMENTS

| | | |
|---|---|---|
| WO | 2014060921 A1 | 4/2014 |
| WO | 2014188347 A1 | 11/2014 |
| WO | 2016193114 A1 | 12/2016 |
| WO | 2017108641 A1 | 6/2017 |
| WO | 2018069330 A1 | 4/2018 |
| WO | 2018115136 A | 6/2018 |

* cited by examiner

METHOD AND SYSTEM FOR PROTECTING A SURFACE AGAINST BIOFOULING

CROSS REFERENCE TO RELATED APPLICATIONS

This application is a U.S. national phase application of International Application No. PCT/EP2019/075007 filed on Sep. 18, 2019, which claims the benefit of EP Application Serial No. 18195677.2 filed on Sep. 20, 2018 and are incorporated herein by reference.

FIELD OF THE INVENTION

The present disclosure relates to methods for preventing fouling, or commonly referred to as anti-fouling, of surfaces and to devices for performing these methods. The disclosure specifically relates to methods and devices for anti-fouling of the hull of ships.

BACKGROUND OF THE INVENTION

Biofouling or biological fouling is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types.

Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances, biofouling creates substantial problems. Machinery stops working, water inlets get clogged, and hulls of ships suffer from increased drag. Hence the topic of anti-fouling, i.e. the process of removing or preventing fouling from forming, is well known.

In industrial processes, bio-dispersants can be used to control biofouling. In less controlled environments, organisms are killed or repelled with coatings using biocides, thermal treatments or pulses of energy. Nontoxic mechanical strategies that prevent organisms from attaching include choosing a material or coating with a slippery surface, or creation of nanoscale surface topologies similar to the skin of sharks and dolphins which only offer poor anchor points.

By way of example, biofouling on the hull of ships causes a severe increase in drag, and thus increased fuel consumption. It is estimated that an increase of up to 40% in fuel consumption can be attributed to biofouling. As large oil tankers or container transport ships can consume up to €200,000 a day in fuel, substantial savings are possible with an effective method of anti-biofouling.

WO 2014/188347 discloses a method and system for preventing biofouling in which all of a surface, or a significant amount of a surface, to be kept clean from fouling (e.g. the hull of a ship) is covered with a layer that emits germicidal light, in particular UV light. Thus, it is known to adopt an optical method, in particular using ultra-violet light (UV). It is well-known that most micro-organisms are killed, rendered inactive or unable to reproduce with sufficient UV light. This effect is mainly governed by the total dose of UV light. A typical dose to kill 90% of a certain micro-organism is 10 mW-hours per square meter.

Ultraviolet (UV) is that part of electromagnetic light bounded by the lower wavelength extreme of the visible spectrum and the X-ray radiation band. The spectral range of UV light is by definition between 100 and 400 nm and is invisible to human eyes. Using the CIE classification the UV spectrum is subdivided into three bands:

UVA (long-wave) from 315 to 400 nm
UVB (medium-wave) from 280 to 315 nm
UVC (short-wave) from 100 to 280 nm Various light sources for generating UV are known, such as low-pressure mercury discharge lamps, medium pressure mercury discharge lamps and dielectric barrier discharge lamps.

A preferred option, for example as proposed in WO 2014/188347 is low cost, lower power UV LEDs. LEDs can generally be included in smaller packages and consume less power than other types of light sources. LEDs can be manufactured to emit (UV) light of various desired wavelengths and their operating parameters, most notably the output power, can be controlled to a high degree. A suitable germicidal dose can easily be achieved with existing UV LEDs.

Most of the lighting panels are always underneath the water level. However, water panels close to the water level can partly emit light above the water level. This depends on the draft of the ship. The UV-C light intensity propagated through the air in close proximity e.g. than 2 m) may then be above the safety limit for maximum exposure to humans.

WO 2016/193114 discloses a solution to this problem in which a water switch is closed to enable the supply of current to the light sources. The water switch makes use of the electrical conductivity of the water to form a galvanic coupling between switch terminals.

However, this approach means that the advantages of full galvanic isolation of the lighting circuit from the vessel and from the water is sacrificed. The galvanic contacts with the sea water will have issues with water ingress but also they are less safe for electrical safety isolation and erosion of the lighting panel due to gas formation through electrolysis.

There remains a need for an improved way to controlling the light to prevent actuation of light sources which are not submerged in water.

SUMMARY OF THE INVENTION

The invention is defined by the claims.

According to examples in accordance with an aspect of the invention, there is provided an anti-fouling lighting panel for mounting over a surface to protect the surface against biofouling while the surface is submerged in water, comprising:

a light source arrangement;

a non-contact water sensor for sensing water thereby to detect whether or not the light source arrangement, or a portion of the light source arrangement, is submerged in water; and a controller for controlling the light source arrangement, or the portion of the light source arrangement, in dependence on the water sensor output.

This lighting panel thus incorporates a water sensor so that the light output may be controlled in dependence on whether there is water over the light source arrangement (or portions thereof). This saves power when the light source output is not needed, and prevents light output through air. Air results in a lower attenuation of the light output, and it may be desirable to prevent this light output reaching objects (such as people) sufficiently close to the surface that they would be illuminated by the light output.

The term "non-contact" means the sensor, in particular electrically conductive components of the sensor, is not in contact with the water to be sensed. The sensing is therefore based on changes in dielectric permittivity, magnetic permeability or optical characteristics in the vicinity of the sensor, but not in contact with the sensor. Thus, the sensing may be based on non-contact remote sensing of the water. The sensing does not make use of the electrical conductivity of the water, but instead relies on other properties which may be interrogated remotely, using electric fields, magnetic fields, or optical illumination. This avoids the need to protect the sensor components from the salt water. Instead, the same protective material surrounding the light sources may be used to protect the water sensor.

Thus, a protective outer coating (which will be in contact with the water being sensed) should not be considered to be part of the sensor. The lighting panel thus comprises a protective electrically insulating layer between the sensor and the water to be sensed. This electrically insulating layer may comprise one side of an encapsulation which surrounds the lighting panel.

Preferably, the controller is adapted to switch off the light source arrangement, or the portion of the light source arrangement, when not submerged in water. Thus, no light output is provided through air. An alternative is to reduce the intensity, but not fully turn of the light source arrangement (or portion thereof).

The light source arrangement may comprise a plurality of rows of light sources, each row comprising one of said portions of the light source arrangement, wherein a water sensor is provided for each row. The rows are for example intended to be horizontal in use, so a water level e.g. around the hull of a ship will result in different rows of light sources being submerged, depending on the loading of the ship and the draft of the ship. Thus, the light output may be dynamically controlled.

The water sensor may comprise a capacitive sensor, comprising a sense pad, a ground electrode, and a capacitance readout circuit. The capacitance which is read out will be influenced by the presence of water. In particular, the ground electrode and sense pad are designed such that the presence or absence of water will make a material and measurable difference to the permittivity arising between the ground electrode and the sense pad.

The water sensor may instead comprise an inductive sensor, comprising an oscillator circuit, a sensor coil, a ground shield having an opening which is exposed to water when the water sensor is submerged, and a frequency detector circuit. The presence or absence of water in the vicinity of the opening then changes a magnetic coupling and hence an oscillation frequency.

The water sensor may instead comprise an optical sensor. For example a reflection amount of a generated light output may depend on the presence or absence of water. For example, total internal reflection of emitted light may illuminate a sensor if the exposed surface is contacted by air, whereas the emitted light may propagate into water if the exposed surface is contacted by water.

The lighting panel may further comprise an inductive power receiver comprising one or more windings for alignment with one or more primary windings of an inductive power transmitter. Thus, the lighting panel is powered by wireless inductive energy transfer.

The invention also provides an anti-fouling lighting system comprising:
an inductive power transmitter for mounting over the surface and comprising one or more primary windings; and
a lighting panel as defined above for mounting over the inductive power transmitter, and comprising an inductive power receiver comprising one or more windings for alignment with the one or more primary windings.

This system creates a galvanically isolated transformer between the power source and the lighting panel.

The inductive power transmitter is for example for mounting against the surface and the lighting panel is for mounting over the inductive power transmitter. The galvanically isolated lighting panel is thus the outer layer.

The inductive power transmitter may comprise an elongate power strip, and the lighting panel comprises an edge region which overlaps the elongate power strip, the inductive power receiver being formed in the edge region. Thus, the coil or coils take up a relatively small area of the lighting panel. A grid may be formed of the power strips (e.g. arranged vertically) and lighting panels (e.g. arranged horizontally).

The inductive power transmitter for example comprises a ferrite sheet below the primary windings, hence between the surface to be protected and the windings. The system efficiency can thus be kept high, e.g. close to 50%. The ferrite sheet is between the surface, e.g. a ship's hull, and the inductive transformer primary windings, to prevent Eddy currents through the conductive hull (or other conductive layer which defines the surface to be protected).

The inductive power receiver for example comprises secondary windings formed on or in a printed circuit board. The PCB material is typically an absorber for the UV light generated, so it should have a smallest possible area. It should also be thin to to maintain flexibility.

The lighting panel for example has a thickness of less than 5 mm, for example less than 4 mm, for example less than 3 mm. This thickness typically includes the printed circuit board and a protective coating.

For example, the lighting panel comprises a silicone coating. This coating may perform an optical function, e.g. light guiding, as well as a protective function. It may be selected to have relative high transparency to the UV light generated.

The inductive power transmitter for example comprises a resonant circuit with a resonant frequency of 50 kHz to 1 MHz, for example 50 kHz to 200 kHz, for example 60 kHz to 90 kHz.

The light source arrangement for example comprises an array of UV-C LEDs with wavelength between 270 nm and 280 nm.

The system may comprise a plurality of inductive power transmitters and a plurality of lighting panels. One inductive power transmitter may be associated with one or more lighting panels.

The invention also provides a method of protecting a surface against biofouling when the surface is submerged in water by operating a light source arrangement to generate anti-fouling light, the method comprising:
sensing water by non-contact sensing thereby to detect whether or not the light source arrangement, or a portion of the light source arrangement, is submerged in water; and
controlling the light source arrangement, or the portion of the light source arrangement, in dependence on the water sensor output.

The method may comprise switching off the light source arrangement, or the portion of the light source arrangement, when not submerged in water.

The light source arrangement may comprise a plurality of rows of light sources, each row comprising one of said portions of the light source arrangement, wherein the method comprises sensing water in the vicinity of each row.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an anti-fouling lighting system used for protecting a surface against biofouling while the surface is submerged in water. A non-contact water sensor is used for sensing water thereby to detect whether or not the light source arrangement, or a portion of the light source arrangement, is submerged in water. The light source arrangement, or the portion of the light source arrangement, is controlled in dependence on the water sensor output.

Figure 1:
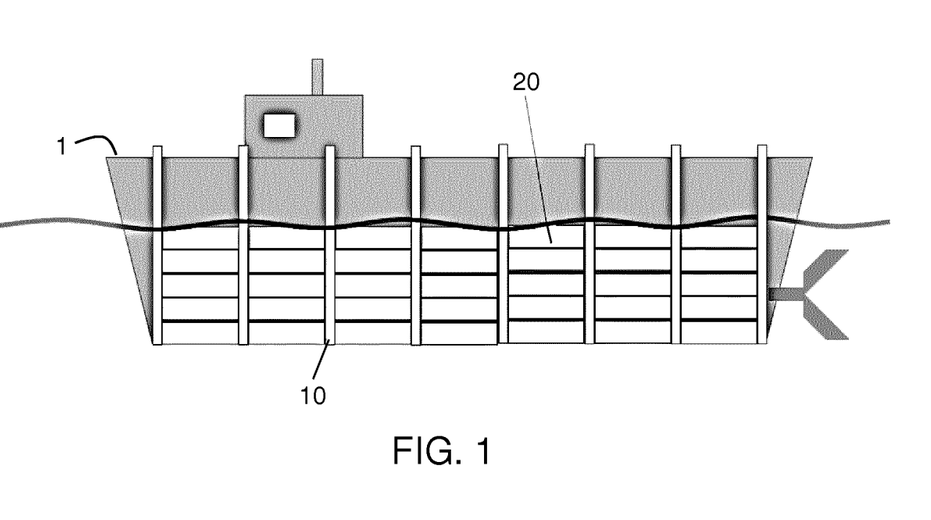
FIG. 1 shows an anti-fouling lighting system applied to a ship for protecting the surface of the ship in contact with water, i.e. the hull surface.

FIG. 1 shows an anti-fouling lighting system, which may be adapted in accordance with the invention, applied to a ship 1, for protecting the surface of the ship in contact with water, i.e. the hull surface.

The anti-fouling system comprises a set of inductive power transmitters 10 mounted over the surface. They take the form of power feeding lines which extend vertically against the hull. At the upper ends, the feeding lines connect to a source of electric power (not shown). The inductive power transmitters each comprise a set of one or more primary windings. A set of primary windings (whether there is one or more than one winding) is referred to as a primary coil in this document.

A set of lighting panels 20 is also mounted over the surface. The lighting panels each comprise a light source arrangement and an inductive power receiver with a set of one or more secondary windings for alignment with the set of primary windings. A set of secondary windings (whether there is one or more than one winding) is referred to as a secondary coil in this document. Thus, the term "coil" generally is used to denote a set of windings forming one side of a transformer.

As will be clear from the description below, there may be multiple coils on each power feeding line, for example one or more coils along the power feeding line at the location of each lighting panel.

Figure 2:
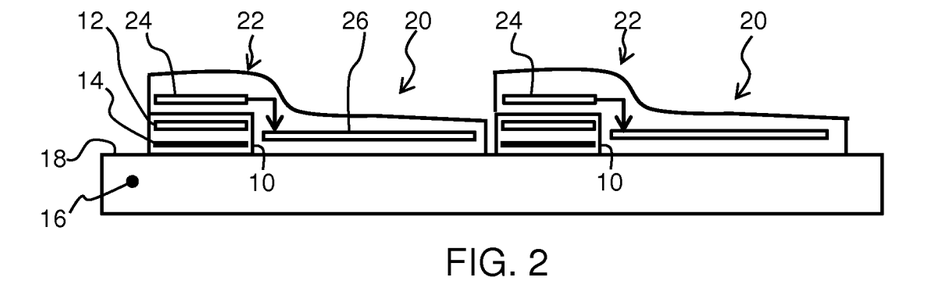
FIG. 2 shows a cross section (in a horizontal plane) through the inductive power transmitters and lighting panels.

FIG. 2 shows a cross section (in a horizontal plane) through the power feeding lines (the inductive power transmitters 10) and through the lighting panels 20. The inductive power transmitters comprise a primary coil 12 and a ferrite sheet 14 between the windings of the primary coil and the metal of the hull 16 of the ship. The surface 18 of the hull is the surface to be protected from fouling. The ferrite sheets prevent Eddy currents in the metal of the ship's hull 16 thereby increasing the efficiency of energy transfer.

In the example shown, the surface 18 is essentially fully covered by the lighting panels. Thus, the surface 18 is protected by the lighting panels, and it is the exposed surface of the lighting panels which is vulnerable to fouling. Thus, the lighting provided by the lighting panels aims to prevent the formation of fouling organisms on the surface of the lighting panels.

However, this is still to be understood as forming a system for protecting the hull surface against biofouling (in that without the lighting system, the hull surface will suffer from biofouling).

An alternative arrangement for example may have lighting panels which only cover a small fraction of the surface to be protected, and the light is directed or guided towards the surface to be protected. In such a case, a major part of the hull surface is indeed exposed to water and therefor susceptible to biofouling.

In the example shown in FIG. 2, the inductive power transmitters 10 are mounted against the hull surface 18 and the lighting panels 20 are mounted over the inductive power transmitters.

In particular, an edge region 22 of each lighting panel 20 overlaps the feeding lines. The lighting panels 20 each have a secondary coil 24 located in this edge region, and a light source arrangement 26.

The secondary windings are aligned with the primary windings to provide inductive power transfer. The wirelessly transmitted power is used by the lighting panels 20 to power the light source arrangements 26.

The primary coils may be formed on or within a printed circuit board of the feeding lines, and the secondary coils may also be formed on or within a printed circuit board of the lighting panel. The light source arrangement may also be formed on a printed circuit board, which may be separate to, or the same as, the printed circuit board of the secondary coils. A shared flexible printed circuit board may for example allow the lighting panels to adapt to the contour of the underlying feeding lines. Instead, there may be separate printed circuit boards in the lighting panel and an electrical connection between them.

Alternatively, the light source arrangement may be formed as a wire grid structure. This reduces the PCB area since a PCB is needed only for the secondary coils.

The printed circuit boards are not shown in the figures, to keep the shown structure simple.

The primary coils of the inductive power transmitters 10 may for example be supplied with a 100 kHz to 150 kHz sinewave during operation of the light emitting system. To compensate for a capacitive leakage current to the hull 16 at the position of the feeding lines, the feeding lines may further be provided with a capacitor to implement a low pass filter. This is for example of interest if high efficiency switched amplifiers are used to generate the AC supply. In such a case, the low pass filter is used to residual higher frequency harmonics of the amplifiers.

An alternative is to use a resonant circuit to generate the AC supply. For example, each feeding line may comprise a resonant circuit, based on a capacitive resonant circuit, with a resonance in the range 60 kHz to 90 kHz.

Generally, the frequency of operation (resonant or driven) may be in the range 50 kHz to 1 MHz, for example 50 kHz to 200 kHz, for example 60 kHz to 90 kHz.

Figure 3:
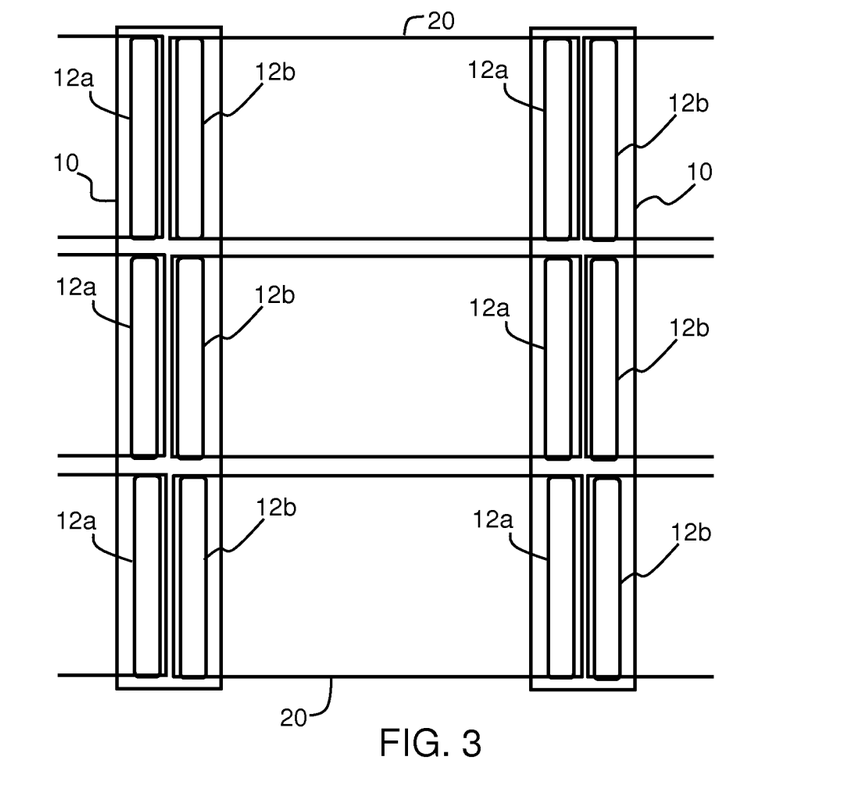
FIG. 3 shows the coil arrangements in more detail.

FIG. 3 shows the coil arrangements.

The example of FIG. 2 has the lighting panels overlapping an associated feeding line at one edge. In FIG. 3, the lighting panels 20 overlap feeding lines 10 at both lateral edges, and each feeding line 10 has pairs of primary coils arranged along its length. One coil of a pair is for powering a lighting panel to one side and the other coil of the pair is for powering a lighting panel to the other side. In this way, each lighting panel is supplied by power from both sides.

All coils of the feeding lines can have the same phase, which contributes to electric redundancy of the light emitting system 40. The light source arrangements 26 can still function in their entirety if a feeding line is broken. In that respect, the feeding lines may be designed to deliver electric power at an increased level of two times a normal level.

Thus, there may be one coil assembly (i.e. primary coil and secondary coil) per lighting panel (FIG. 2) or two coil assemblies per lighting panel (FIG. 3).

There may be between 2 and 50 lighting panels per feeding line, for example 20 rows of individual tiles connected to a feeding line.

In the example shown, the feeding lines extend in a substantially vertical orientation along the side of the ship. However, any suitable arrangement of feeding lines is possible. The feeding lines may for example cover welding seams and/or other surface irregularities of the ship's hull.

Figure 4:
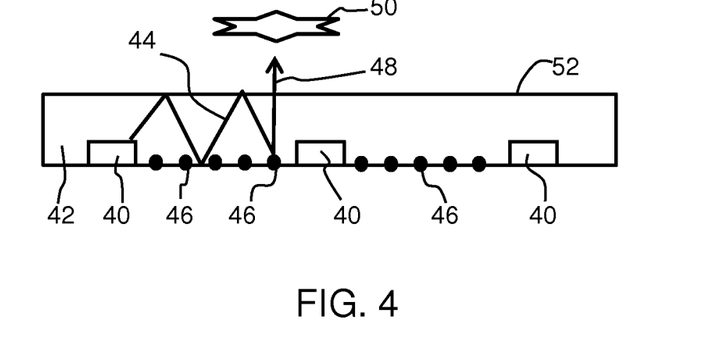
FIG. 4 shows an example of the structure of the lighting panel.

FIG. 4 shows an example of the structure of the lighting panel 20, having a plurality of light sources 40 which in this example are side-emitting UV-C LEDs, wherein the light is emitted primarily from a side of the LED, and more or less parallel to the surface. The light sources 40 are encapsulated in a liquid-tight optical medium 42 to guide at least part of the light 44 emitted from the light sources 40 via total internal reflection through the optical medium.

Optical structures 46 are provided to disrupt the total internal reflection and scatter light, and then guide the scattered light 48 out of the optical medium 42 towards a target for the light, which is an area where a biofouling organism is present.

A biofouling organism on the surface 52 will directly receive the light scattered light 48 before it enters the water.

Furthermore, some of the internally scattered light 48 that does enter the water will encounter external scattering sites. This creates illumination 50 within the water, some of which will also reflect back to the surface 52 of the lighting panel 20 where biofouling is to be prevented.

The illumination means that single cell bio-mechanisms at the surface 52 will stop growing and dividing, and will therefor die under influence of the UV-C light.

The optical medium is relatively thin so that the lighting panel may be considered to be a two-dimensional structure. The optical structures 46 to scatter light may be spread in one or more portions of the optical medium material, possibly throughout all of it, and the light output may be generally homogeneous or else localized.

Internal scattering centers with different structural properties may be combined to provide optical and well as structural characteristics, such as resistance to wear and/or impact. Suitable scatterers comprise opaque objects but largely translucent objects may be used as well, e.g. small air bubbles, glass and/or silica; a requirement is merely that a change in refractive index occurs for the wavelength(s) used.

The principle of light guiding and spreading light over a surface is well-known and widely applied in various fields. Here, the principle is applied to UV light for the purpose of anti-fouling.

To maintain the conditions for total internal reflection, the index of refraction of the light guiding material should be higher than that of the surrounding medium. However, the use of (partly) reflecting coatings on the light guide and/or the use of the reflective properties of the protected surface, e.g. the hull of a ship, itself can also be used to establish the conditions for guiding the light through the optical medium.

In the example above, the lighting panels form a new surface over the surface to be protected, and light is directed outwardly from the surface to be protected. However, an alternative is for the lighting panel to be spaced over the surface to be protected and to direct light back towards the surface to be protected.

A small air gap may then be introduced between the light source arrangement of the lighting panel and the surface to be protected. UV light may travel better, with less absorption, in air than in an optical medium, even when this optical medium is designed as a light guiding material.

As most materials have a (very) limited transmittance for UV light, care has to be taken in the design of the optical medium. As a result, a relatively fine pitch of low power LEDs can be chosen, to minimize the distance light has to travel through the optical medium.

In one example, the optical medium 42 comprises a silicone, and one which is designed to have good UV-C transparency.

A solid encapsulation may be used, as shown in FIG. 4. However, a hollow structure may instead be used, such as a silicone mat with spacers that keep it a small distance away from the protected surface. This creates air channels, through which the UV light can propagate with higher efficiency. Use of gas filled channels provided by such structures allows distributing the UV light over significant distances in a optical medium of material that would otherwise absorb the UV light too strongly to be useful for anti-fouling. Similarly, separate pockets may be formed.

Figure 5:
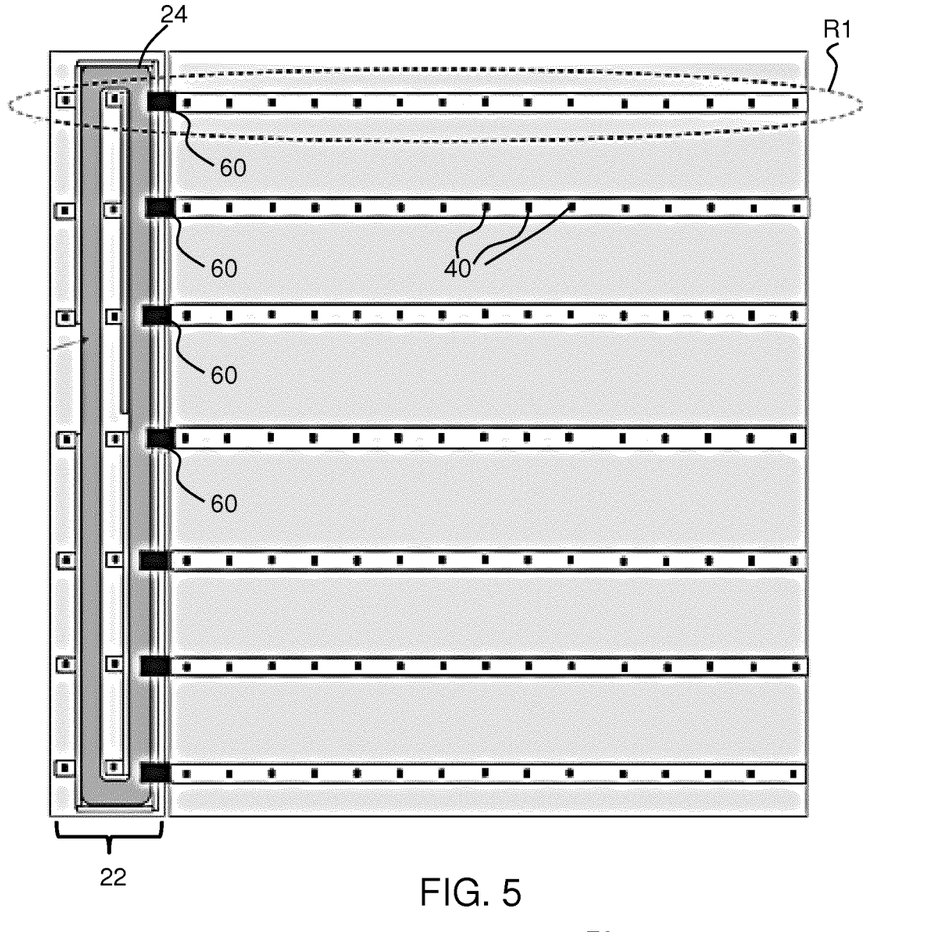
FIG. 5 shows a lighting panel viewed from the light emitting surface.

FIG. 5 shows a lighting panel 20 viewed from the front. The lighting panel comprises a two dimensional array of the LEDs 40 and the primary coil 24 at an edge region 22.

The LEDs 40 are arranged as a plurality of rows. In accordance with the invention, the panel or more preferably each row of LEDs within the panel, has a water sensor 60.

The LEDs 40 are provided on a printed circuit board, and the printed circuit board traces also define the windings of the secondary coil 24. The water sensor may be provided on the PCB, making use of a mounted components and/or components formed by PCB traces.

The output of the water sensor is used to control the light source arrangement, in particular the associated row of light sources of the light source arrangement, in dependence on the water sensor output.

The water sensor output may for example directly control an interrupt switch, in which case the switch functions as a controller. Alternatively, there may be a separate controller, such as an IC, to which the sensor outputs are provided. The controller IC then provides control signals to isolating switches or it may provide an analog control of the light output.

In most simple implementation, a simple MOSFET circuit is used as a switch, and the output of the water sensor controls the gate of the MOSFET circuit. The MOSFET circuit may then be considered to be the controller.

The controller (whether a switch or controller IC) is preferably adapted to switch off the light source arrangement, or the portion of the light source arrangement, when not submerged in water. However, an alternative is to reduce the light output intensity, for example by increasing a series impedance in series with the light sources 40 in the row.

The water sensor does not rely on physical contact with the water, and hence does not make use of the electrical conductivity of the water. Instead, it is a non-contact sensor which relies on changes in an electrical field, magnetic field or optical characteristics which depend on the presence of, or absence of, water in the vicinity of the sensor.

Figure 6:
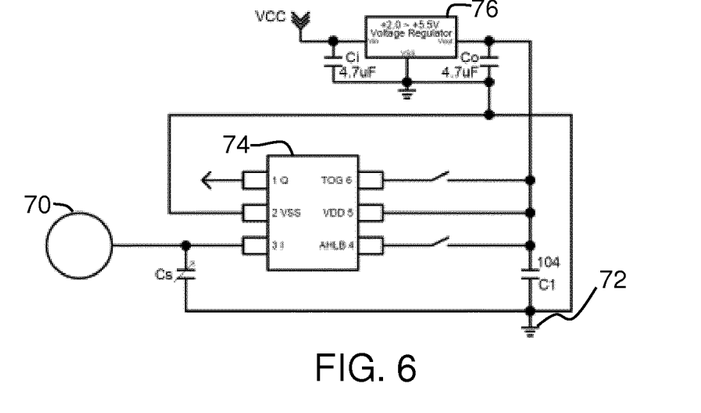
FIG. 6 shows a first example of non-contact water sensor circuit based on capacitance sensing.

A first example of a possible water sensor is a capacitive sensor. An example is shown in FIG. 6, comprising a sense pad 70 and a ground electrode 72, and a capacitance readout circuit 74. Such readout circuits are well known, for example for touch pad sensing.

An input voltage is regulated by a voltage regulator 76 and delivered to a reference capacitor C1. The voltage across a capacitance to be sensed Cs is provided to a sensing terminal of the readout circuit 74.

The sense pad does not need to be in contact with the water. Instead, as long as the presence or absence of water influences the capacitance between the sense pad 70 and the ground electrode 72, the water presence can be detected.

Figure 7:
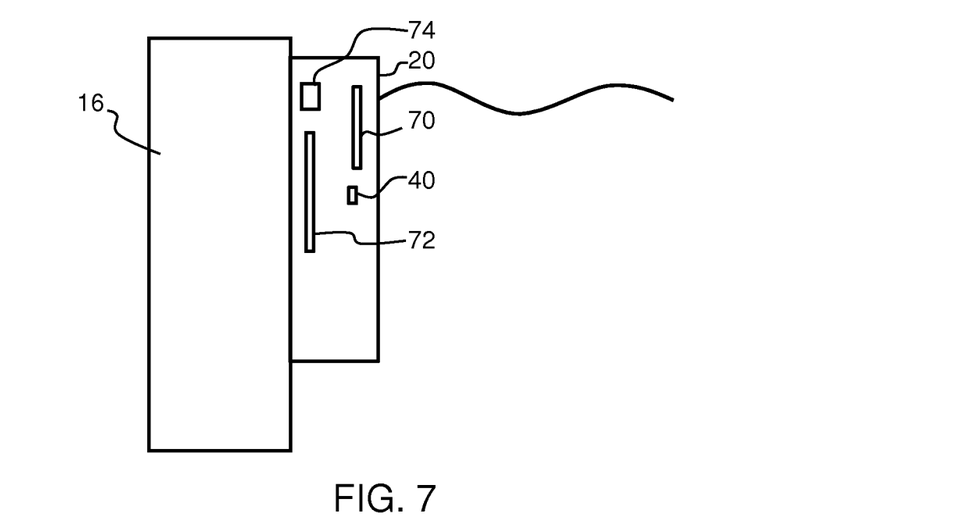
FIG. 7 shows the components of FIG. 6 embedded in the lighting panel.

FIG. 7 shows the arrangement of the components in the lighting panel. The sense pad 70 is buried in the optical material of the panel, but the presence of water at the surface influences the dielectric coupling between the sense pad 70 and the ground electrode 72.

Figure 8:
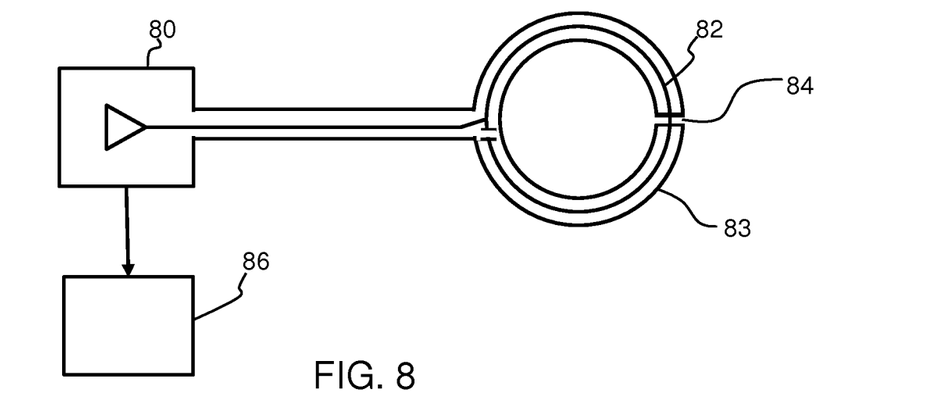
FIG. 8 shows a second example of non-contact water sensor circuit based on magnetic inductance sensing.

A second example of a possible water sensor is an inductive sensor. An example is shown in FIG. 8. The sensor comprises an oscillator circuit 80 and a sensor coil 82. The sensor coil is covered by a conductive ground shield 83 (forming a Faraday shield) having an opening 84. This opening 84 is exposed to water when the water sensor is submerged. However, the sensor loop is not exposed for direct contact with the water. There is an insulating protective layer between the coil and the water, i.e. the optical material in which the lighting panel is encapsulated. Thus, direct contact between the water and any electrically conducive parts of the sensor such as the sensor coil, is avoided. The sensor loop functions as a loop antenna. The oscillator for example runs between 50 MHz and 500 MHz. A change in magnetic permeability in the vicinity of the gap causes a shift in frequency, which is detected by a frequency detector circuit 86.

The sensor functionality may be incorporated into an integrated circuit or it may be formed using tracks of the PCB.

Further details of this sensing approach in a different technical field may be found in WO 2018/202486. The frequency shift is the result of magnetic fields induced by Eddy currents. These Eddy currents depend on the magnetic permeability (i.e. magnetic impedance) of the material in the vicinity of the opening 84. Thus, the sensor may be considered to be a magnetic impedance sensor.

Figure 9:
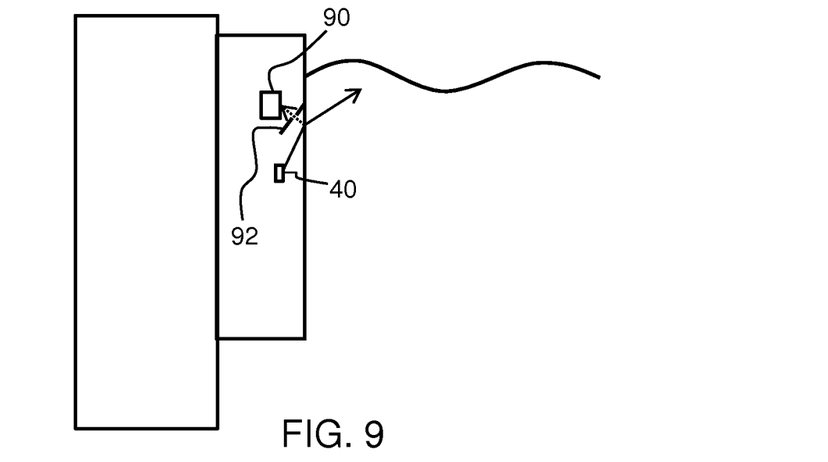
FIG. 9 shows a third example of non-contact water sensor circuit based on optical sensing.

A third example of a possible water sensor is an optical sensor. An example is shown in FIG. 9.

The sensor comprises a sensor light source 40 and an optical detector 90. The light source 40 may be one of the UV-C light sources, or it may be a dedicated light source selected specifically for the optical sensing function.

The optical detector 90 is for receiving light reflected from the water or air, or from the refractive index boundary to the water or air. The light detector is covered by a portion of the encapsulation.

For example, light emitted at a certain angle may propagate into water or it may be reflected by the refractive index interface when air is present. Thus, detection of total internal reflection may be used to detect the presence of an air interface, and thereby detect when the lighting panel is not submerged. If a thin layer of water is present over the sensor (even though the sensor is not submerged), total internal reflection may still be detected from the outermost water-air interface. Thus, the sensor does not need to be totally dry to detect air.

A directional filter 92 may ensure that only light in the required sensing direction is detected. Similarly, a color filter may be used to filter light of a particular wavelength to correspond to a dedicated light source 40 of the optical sensor.

An optical sensor may instead detect back scattering (rather that reflection from a refractive index boundary). Back scattering from water will create a higher light intensity signal than back scattering from air.

Thus, different optical sensing approaches are possible.

Thus, it can be seen that there are three main non-contact methods to determine the water level next to the ship and to switch off light sources as a result. These are based on capacitive sensing, inductive sensing and optical sensing (which may use the UV-C light or other light specifically for the optical sensing).

A typical secondary side current is 0.1 A and a typical desired secondary side voltage is around 40V. For safety, a maximum voltage of 50V rms (by way of example only) may be considered. The system is designed or operate below the maximum voltage, taking into account all the characteristics of the inductive coupling and the spreading of currents. For a given operating voltage, the required current depends on the required power. A higher voltage enables a lower current and vice versa.

The feeding lines for example make use of a PCB with thickness of less than 1 mm, for example 0.5 mm, created a molded structure thickness of around 3 mm.

The lighting panels for example have a PCB thickness of 0.8 mm, and the total thickness with the silicone of below 5 mm, for example in the range 2 mm to 4 mm.

The invention is of particular interest for marine objects although not limited to objects for use in seawater, but also in any type of water that is known to contain biofouling organisms. Examples of marine objects include ships and other vessels, marine stations, sea-based oil or gas installations, buoyancy devices, support structures for wind turbines at sea, structures for harvesting wave/tidal energy, sea chests, underwater tools, etc.

In preferred examples, the light sources are UV LEDs as explained above. A grid of UV LEDs may be encapsulated in a liquid-tight encapsulation, of which silicone is only one example. The UV LEDs may be electrically connected in a series and/or parallel arrangement. The UV LEDs are for example packaged surface mount LEDs, in which case they already may include an optical element to distribute the light emitted from the LED package across a wide emission angle. In other embodiments, the UV LEDs may be LED dies, typically not comprising optical elements but being significantly thinner than packaged LEDs. As an example, LED dies could be picked and placed onto a surface of the optical medium The silicone material can be selected to provide optical transmission for UV light with little loss compared to other materials. This is in particular the case for shorter wavelength light, e.g. UV light with wavelengths below 300 nm. A particularly efficient group of silicone materials is, or at least comprises, so-called methyl silicones, according to the general chemical formula $CH_3[Si(CH_3)_2O]_nSi(CH_3)_3$, with "n" indicating any suitable integral.

Silicone materials are also flexible and resilient so that they are robust, durable and capable of withstanding compression such as due to bumps, collisions etc. of objects against the surface, e.g. bumping of a ship against a quay. Furthermore, deformation due to temperature fluctuation, pounding by waves, flexion of the ship over swell etc. may be accommodated.

At least part of light emitted by the one or more light sources may be spread in a direction having a component substantially parallel to the surface to be protected. This facilitates distributing the light over significant distances along the protected surface, or the application surface of the foil, which assists in obtaining a suitable intensity distribution of the anti-fouling light.

A wavelength conversion material may be comprised in the optical medium and at least part of the anti-fouling light may be generated by photo-exciting the wavelength conversion material with light having a first wavelength causing the wavelength conversion material to emit the anti-fouling light at another wavelength. The wavelength conversion material may be provided as an up-conversion phosphor, quantum dots, nonlinear media such as one or more photonic crystal fibers etc. Since absorption and/or scattering losses in the optical medium for light of different, mostly longer, wavelengths than UV light tend to be less pronounced in the optical media, it may be more energy-efficient to generate non-UV light and transmit that through the optical medium and to generate UV anti-fouling light at or near the desired location of use thereof (i.e. emission form the surface into the liquid environment).

One example described above makes use of side-emitting LEDs and optical scattering sites. However, light spreading arrangements may be used to create the sideways light. For example, a cone may be arranged in the optical medium and positioned opposite the light source, where the opposing cone has a surface area with a 45° angle perpendicular to the protected surface for reflecting light emitted by the light source perpendicular to said surface in a direction substantially parallel to said surface.

The LEDs may be DC driven. However, a pair of back to back parallel LEDs may be driven by an AC drive signal.

As mentioned above the LEDs are preferably mounted on a PCB, and PCB tracks (on the PCB surface or internally within layers of the PCB) form the receiver coil. However, the LED grid may instead be formed by connecting LEDs to a connection nodes of a freestanding wire structure by soldering, gluing or any other known electrical connection technique. This may be combined with a secondary coil on a smaller PCB.

The invention can be applied to a wide variety of fields. Almost any object coming into contact with natural water, will over time be subject to biofouling. This can hinder e.g. water inlets of desalination plants, block pipes of pumping stations, or even cover the walls and bottom of an outdoor pool. All of these applications would benefit from the presently provided method, lighting modules and/or system, i.e. an effective thin additional surface layer, which prevents biofouling on the entire surface area.

Although UV light is the preferred solution, other wavelengths are envisaged as well. Non-UV light (visible light) is also effective against biofouling. Typical micro-organisms are less sensitive to non-UV light than to UV light, but a much higher dose can be generated in the visible spectrum per unit input power to the light sources.

UV LEDs are an ideal source for thin light emitting surfaces. However, UV sources other than LEDs can also be used, such as low pressure mercury vapor lamps. The form factor of these light sources are quite different; mainly the source is much bigger. This results in different optical designs, to distribute all the light from a single source over a large area. Further, a significant contribution of light in desired wavelengths and/or wavelength combinations may be produced. Instead of using a thin layer that emits UV light outward in a direction away from the protected surface in order to avoid bio-fouling, biofouling could potentially also be removed by applying UV light from the outside in the direction of the protected surface, as explained above. The lighting panel may instead emit anti-fouling light both in directions towards and away from the surface to be protected.

In the examples above, the lighting panel overlaps the feeding lines. This provides galvanic isolation between the power supply and the structure which is exposed to the water. The lighting panel also protects the feeding lines. Instead, the feeding lines may be provided over the lighting panels. A separate electrical isolation may be provided (e.g. at the top of the feeding lines). The surface of the feeding lines will then be susceptible to biofouling, so it should then be ensured that light reaches the surface of the feeding lines, either by transmission through the feeding lines or by reflection or waveguide transmission within the lighting panels. Thus, the inductive power transmitter and the lighting panel are both for mounting over the surface, but in either order.

The lighting panels for example have a length (along the horizontal row direction) in the range 1 m to 5 m and a height (along the vertical column direction) in the range 50 cm to 150 cm. For example a small panel dimension may be 600 mm×1200 mm and a large panel dimension may be 1 m×4 m. An example area to be covered, e.g. one side of a ship hull, may be of the order of 100 m length by 10 m height.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. An anti-fouling lighting panel for mounting over a surface to protect the surface against biofouling while the surface is submerged in water, comprising:
   a light source arrangement comprising a plurality of portions;
   a non-contact water sensor for sensing water to detect whether or not each portion of the light source arrangement, is submerged in water; and
   a controller for controlling each portion of the light source arrangement, in dependence on the water sensor output;
   wherein the water sensor comprises:
   a capacitive sensor, comprising a sense pad, a ground electrode, and a capacitance readout circuit; or
   an inductive sensor, comprising an oscillator circuit, a sensing coil, a ground shield having an opening which is exposed to water when the water sensor is submerged, and a frequency detector circuit.

2. The lighting panel of claim 1, wherein the controller is adapted to switch off the portion of the light source arrangement, when not submerged in water.

3. The lighting panel of claim 1, wherein the light source arrangement comprises a plurality of rows of light sources, each row comprising one of said portions of the light source arrangement, wherein a water sensor is provided for each row.

4. The lighting panel of claim 1, further comprising:
   an inductive power receiver comprising one or more windings for alignment with one or more primary windings of an inductive power transmitter.

5. An anti-fouling lighting system comprising:
   an inductive power transmitter for mounting over the surface and comprising one or more primary windings; and
   a lighting panel as claimed in claim 1 for mounting over the inductive power transmitter, and comprising an inductive power receiver comprising one or more windings for alignment with the one or more primary windings.

6. The anti-fouling lighting system of claim 5, wherein the inductive power transmitter comprises an elongate power strip, and the lighting panel comprises an edge region which overlaps the elongate power strip, the inductive power receiver being formed in the edge region.

7. The anti-fouling lighting system of claim 5, wherein the inductive power transmitter comprises a ferrite sheet below the windings.

8. The anti-fouling lighting system of claim 5, wherein the lighting panel comprises a printed circuit board at least for the one or more secondary windings and a silicone coating.

9. The anti-fouling lighting system of claim 5, comprising a plurality of inductive power transmitters and a plurality of lighting panels.

10. A method of protecting a surface against biofouling when the surface is submerged in water by operating a light source arrangement to generate anti-fouling light, the method comprising:
    sensing water by non-contact sensing thereby to detect whether or not portions of the light source arrangement are submerged in water; and
    controlling each portion of the light source arrangement, or the portion of the light source arrangement, in dependence on the water sensor output,
    wherein water sensor comprises using:
    a capacitive sensor, comprising a sense pad, a ground electrode, and a capacitance readout circuit; or
    an inductive sensor, comprising an oscillator circuit, a sensing coil, a ground shield having an opening which is exposed to water when the water sensor is submerged, and a frequency detector unit.

11. The method of claim 10, comprising switching off the portion of the light source arrangement, when not submerged in water.

12. The method of claim 10, wherein the light source arrangement comprises a plurality of rows of light sources, each row comprising one of said portions of the light source arrangement, wherein the method comprises sensing water in the vicinity of each row.

* * * * *